United States Patent [19]
Childers et al.

[11] Patent Number: 6,123,738
[45] Date of Patent: Sep. 26, 2000

[54] PROCESS FOR THE PRODUCTION OF LOW COLOR 2,3-EPOXYPROPYLTRIALKYLAMMONIUM HALIDE

[75] Inventors: Laren P. Childers; Dorothy L. Roerden, both of Lake Jackson, Tex.

[73] Assignee: The Dow Chemical Company, Midland, Mich.

[21] Appl. No.: 09/136,713

[22] Filed: Aug. 19, 1998

[51] Int. Cl.$^7$ .................................................. C07D 303/36
[52] U.S. Cl. .............................. 8/102; 8/108.1; 8/115.51; 549/513; 536/45; 536/50
[58] Field of Search ....................... 8/102, 108.1, 115.51, 8/188, 115.61, 115.65; 549/513, 518; 536/45, 50; 252/187.24, 187.1, 187.32

[56] References Cited

U.S. PATENT DOCUMENTS

| | | | |
|---|---|---|---|
| 2,876,217 | 3/1959 | Paschall | 536/50 |
| 3,346,563 | 10/1967 | Shildneck et al. | 536/50 |
| 3,475,458 | 10/1969 | McClure et al. | 549/514 |
| 3,532,751 | 10/1970 | Langhor et al. | 564/292 |
| 4,066,673 | 1/1978 | Doughty et al. | 549/514 |
| 4,450,295 | 5/1984 | van der Mass | 564/294 |
| 4,594,452 | 6/1986 | Reimschuessel et al. | 564/292 |
| 5,006,125 | 4/1991 | Patton et al. | 8/188 |
| 5,637,740 | 6/1997 | Fischer et al. | 549/541 |

FOREIGN PATENT DOCUMENTS 2092150   8/1982   United Kingdom.

OTHER PUBLICATIONS

James D. McClure, "Glycidyltrimethylamminium Chloride and Related Compounds", J. Org. Chem., vol. 35, No. 6, pp. 2059–2061 (1970) (no month available).

D. M. Burness, "Anomlous Reaction of Epichlorohydrin with Trimethylamine", Research Laboratories, Eastman Kodak Company, Rochester, New York vol. 29, pp. 1862–1864, Jul. 1964.

*Primary Examiner*—Caroline D. Liott

[57] ABSTRACT

2,3-Epoxypropyltrimethylammonium chloride having reduced color and method of preparation are disclosed. 2,3-Epoxypropyltrimethylammonium chloride is treated with sodium hypochlorite to reduce its color. 2,3-Epoxypropyltrimethylammonium chloride can be prepared via reaction of trimethylamine and epichlorohydrin. If desired, an aprotic solvent can be used. 2,3-Epoxypropyltrimethylammonium chloride formed in the resultant slurry, must then be isolated via known methods, such as evaporation, extraction, centrifugation, etc, depending upon the other constituents of the slurry and the residual epichlorohydrin removed. The final product is then treated with an effective amount of sodium hypochlorite. The obtained 2,3-epoxypropyltrimethylammonium chloride then is used for, for example, color-sensitive applications such as to produce cationic starch for use in paper manufacture.

12 Claims, No Drawings

PROCESS FOR THE PRODUCTION OF LOW COLOR 2,3-EPOXYPROPYLTRIALKYLAMMONIUM HALIDE

BACKGROUND OF THE INVENTION

The present invention relates to a process for preparing low color 2,3-epoxypropyltrialkylammonium halide, and more particularly, low color 2,3-epoxypropyltrimethylammonium chloride.

Various methods for preparing 2,3-epoxypropyltrimethylammonium chloride are known in the art. However, these known processes yield a product which is yellow in color to various degrees. Some of these methods are described hereinafter.

James D. McClure, J. Org. Chem., Vol.35,No. 6,pp. 2059–2061 (1970), describes a process for the preparation of glycidyltrimethylammonium chloride by reacting epichlorohydrin with trimethylamine. The reaction is illustrated by the following equation:

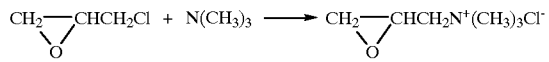

This reaction is best carried out in an aprotic solvent such as ethers, ketones, and esters in which 2,3-epoxypropyltrimethylammonium chloride is insoluble. An excess of epichlorohydrin can be used as solvent as well. Preparation of 2,3-epoxytrimethylpropylammonium bromide by reacting epibromohydrin with trimethylamine is also described in this article.

U.S. Pat. No. 3,475,458 (J. D. McClure) discloses the preparation of crystalline glycidyltrimethylammonium chloride of high epoxide level, useful in the production of starch ethers, by reacting epichlorohydrin and trimethylamine in a solvent selected from saturated hydrocarbon ether, lower alkyl ketone, lower alkyl alkanoate and chlorofom-hydrocarbon mixtures.

U.S. Pat. No. 4,066,673 (J. B. Doughty et al) discloses a process for the preparation of 1,2-epoxy propyl trialkylamine chloride in a methanol solution. Epichlorohydrin is first dissolved in methanol and then a stoichiometric amount of trialkylamine (for example, trimethylamine or triethylamine) in methanol is slowly added thereto.

It is also known to prepare 2,3-epoxypropyltrimethylammonium chloride by a method which involves reacting epoxy compounds, particularly epichlorohydrin, with an acid salt of a trialkylamine, particularly trimethylamine hydrochloride, in aqueous media, followed by treatment with caustic. This method is illustrated by the following equations:

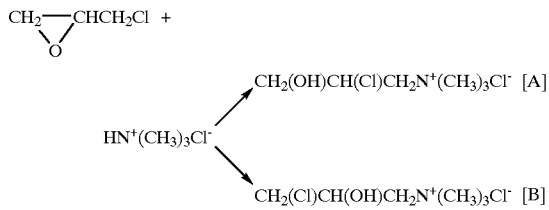

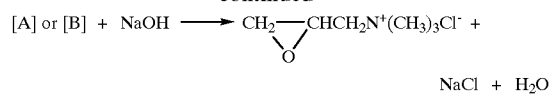

The use of 2,3-epoxypropyltrimethylammonium chloride for preparing cationic starch ethers is also well known. Some of the processes for preparing cationic starch ethers are described hereinafter.

U.S. Pat. No. 2,876,217 (E. F. Paschall) discloses a process for the preparation of starch ethers containing quaternary ammonium substituents by reacting starch with the reaction product of epihalohydrin and a tertiary amine or a tertiary amine salt. The epihalohydrintriethylamine reaction product is obtained by mixing triethylamine and epihalohydrin with water. After agitating the reaction solution for 5 hours at room temperature, the solution is concentrated to a thick syrup under a vacuum. This epihalohydrintriethylamine syrup is added to an alkaline aqueous slurry of starch. The reaction mass is then neutralized with acid and the cationized starch ether recovered.

U.S. Pat. No. 3,346,563 (P. R. Shildneck et al) discloses a process for the preparation of a cationic starch ether by reacting starch and a quaternary halohydrin salt with an alkaline catalyst, the halohydrin being obtained by reacting hypohalous acid with allyl quaternary halide salt of a tertiary amine. This process, is represented by the following equation:

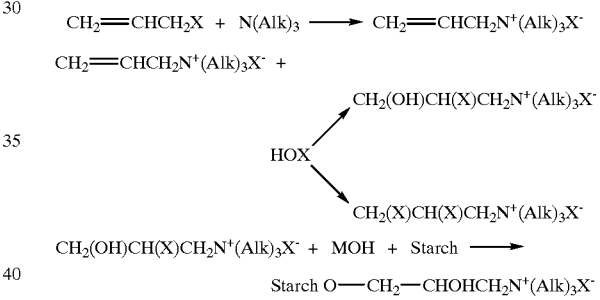

It was postulated that, in the presence of the alkali, an intermediate reaction takes place by which the halohydroxypropyl quaternary ammonium ether is cycled to form in situ the epoxide and that this epoxide reacts with starch.

2,3-Epoxypropyltrialkylammonium halides are reactive cationic quaternary amines. They are readily reactive with most substrates, charged or uncharged, to impart to it a permanent cationic charge. Examples of suitable substrate include, for example, natural cellulosic materials such as starch, flour, guar gum, as well as synthetic materials such as cellulose ethers, polyvinyl alcohol and polymers. In particular, 2,3-epoxypropyltrimethylammonium chloride has been widely commercially used in the manufacture of cationic starches.

2,3-Epoxypropyltrialkylammonium halides also suitably impart a permanent cationic charge to various fibers. Suitable fibers include: (i) natural and regenerated cellulosic fibers such as, for example, cotton, linen, and viscose rayon; (ii) natural and regenerated protein fibers such as, for example, wool, cashmere, and casein; (iii) regenerated fibers such as, for example, cellulose acetate, and cellulose triacetate; (iv) synthetic fibers such as, for example, polyamide, polyester, and polyacrylonitrile.

In addition to 2,3-epoxypropyltrialkylammonium halides aqueous solutions of about 50% to about 70% active 3-chloro-2-hydroxylpropyltrimethylammonium chloride are commercially available for use as quaternizing agents. When this type of the quaternizing agent is used, caustic or other base must be utilized to first convert it to its epoxy form since it is the epoxy form of the quaternizing agent that is the active species for most reactions.

One particular use for these quaternizing agents as reacted with alkaline starch is in the manufacture of paper. The cationic starch is added in the wet-end of a paper process and functions primarily as a dry strength additive. The cationic starch maintains its charge throughout the entire pH range, so that it is usable in acid, neutral, and alkaline papermaking processes. It functions like a charged glue to hold the paper fibers together, and is believed to improve sheet strength by promoting fiber bonding through a combination of ionic bonding with the essentially anionic cellulosic substrates, and also hydrogen bonding. It also finds use in conjunction with internal sizing agents, including alkenyl succinic anhydride ("ASA") and alkylketene dimer ("AKD"), in fine paper applications.

However, in the paper manufacture color and brightness are important qualities. Therefore, raw materials used in production are desirably colorless or of extremely low color. Unfortunately, widely used conventional direct reaction of epichlorohydrin with trimethylamine produces 2,3-epoxypropyltrimethylammonium chloride which has a strong yellow color. When this product is used to make cationic starch, the yellow color may be imparted to the cationic starch and thus to the final paper product. The color of 2,3-epoxypropyltrimethylammonium chloride can be reduced slightly by lowering the temperature or increasing the ratio of epichlorohydrin to trimethylamine which are reacted to form the 2,3-epoxypropyltrimethylammonium chloride. However, both of these alternatives increase capital and operating costs, and the lower temperatures also slow down the reaction. Increasing the epichlorohydrin to trimethylamine ratio also tends to reduce yield and require more recycle epichlorohydrin for a given reactor.

There is a perceived need in the industry for the 2,3-epoxypropyltrialkylammonium halide product which is devoid of color or has reduced color so that, upon application, less color is imparted to the cationic starch and thence to the paper, or other, final product.

SUMMARY OF THE INVENTION

The present invention provides a process for eliminating or reducing the color of 2,3-epoxypropyltrialkylammonium halide prepared by conventional methods.

In one embodiment the present invention is a process for eliminating or reducing color of 2,3-epoxypropyltrialkylammonium halide which process comprises treating an aqueous solution of colored 2,3-epoxypropyltrialkylammonium halide with an effective amount of an alkali metal salt of hypochlorous acid, hypochlorous acid or chlorine.

In another embodiment, the present invention is 2,3-epoxypropyltrialkylammonium halide having clear or reduced color prepared by treating an aqueous solution of colored 2,3-epoxypropyltrialkylammonium halide with an effective amount of an alkali metal salt of hypochlorous acid, hypochlorous acid, or chlorine.

In another embodiment, the present invention is a process for producing a cationic substrate by reacting a substrate with 2,3-epoxypropyltrialkylammonium halide prepared by the process described hereinbefore.

Yet in another embodiment, the present invention is a cationic substrate produced by reacting a substrate with 2,3-epoxypropyltrialkylammonium halide obtained by the process described hereinbefore.

Yet in another embodiment, the present invention is a process for producing a cationic fiber by reacting a fiber with 2,3-epoxypropyltrialkylammonium halide prepared by the process described hereinbefore.

Still in another embodiment, the present invention is a cationic fiber produced by reacting a fiber with 2,3-epoxypropyltrialkylammonium halide obtained by the process described hereinbefore.

DESCRIPTION OF THE PREFERRED EMBODIMENTS

The present invention provides a simple, convenient and relatively inexpensive way to obtain 2,3-epoxypropyltrialkylammonium halide which is essentially clear (water-white) in color or has reduced color and therefore is highly desirable for application in the papermaking industry, as well as in other applications requiring low color.

An aqueous solution of colored 2,3-epoxypropyltrialkylammonium halide is treated with an effective amount of an alkali metal salt of hypochlorous acid, hypochlorous acid, or chlorine to (eliminate or reduce its color.

Any alkali metal salt of hypochlorous acid can be used in the present invention; however, sodium hypochlorite is preferred. Chlorine can be used either as a gas or as an aqueous solution.

In the context of the present invention, an effective amount of an alkali metal salt of hypochlorous acid, hypochlorous acid or chlorine is an amount which is capable of providing from about 200 to about 15,000, preferably from about 400 to about 10,000, more preferably from about 600 to about 5,000, most preferably from about 600 to about 2,500, parts per million (ppm) of active chlorine in the solution.

While it is preferable to add an alkali metal salt of hypochlorous acid, hypochlorous acid, or chlorine to the aqueous solution of 2,3-epoxypropyltrialkylammonium halide at approximately room temperature for the sake of convenience, it is possible to use temperatures from about 0° C. to about 80° C. and pressures from about 0 to about 100 psig.

2,3-Epoxypropyltrialkylammonium halide is conveniently prepared by a known process comprising the steps of (1) reacting trialkylamine with epihalohydrin to form a slurry containing solid 2,3-epoxypropyltrialkylammonium halide; (2) extracting 2,3-epoxypropyltrialkylammonium halide from the slurry using water; and (3) removing residual amounts of epihalohydrin from the aqueous solution of 2,3-epoxypropyltrialkylammonium halide. This product has yellow color.

Raw materials (epihalohydrin and trialkylamine) for this process are generally commercially available and reaction conditions are relatively mild, yet yields are high.

The ratio of the trialkylamine to the epihalohydrin is preferably stoichiometric or with an excess of epihalohydrin to serve as a solvent. If a stoichiometric or less than stoichiometric ratio of trialkylamine to epihalohydrin is selected, an additional aprotic liquid is desirably used as a solvent.

Any aprotic liquid can be used in the above process. Conveniently, the aprotic liquid used in the above process includes acetone, tetrahydrofuran, dimethoxyethane, ethylacetate, and mixtures thereof.

Epibromohydrin, epichlorohydrin, epiflourohydrin and epiiodohydrin are all useful in the above process. Epichlorohydrin is preferred epihalohydrin.

Any known trialkylamine can be used in the above process. The trialkylamine can contain same or different alkyl groups. Preferred are those which contain same alkyl groups. Trialkylamines in which the alkyl group contains from 1 to 6 carbon atoms are preferred. Trimethylamine and triethylamine are further preferred trialkylamines.

The order of addition of the materials is not important, but if excess epihalohydrin is used to comprehend both reactant and solvent, it is preferable to charge that component to the reactor first, and then add the trialkylamine thereafter with stirring. Reaction temperature is normally from −10° C. to about 50° C. Reaction time can vary from about 1 hour to about 48 hours.

Once this reaction has taken place a slurry of the reaction product in the solvent is formed. The reaction product is 2,3-epoxypropyltrialkylammonium halide.

This product is then extracted, preferably by dissolving it in water. Water is preferably added in an amount to give a 70 percent concentration of 2,3-epoxypropyltrialkylammonium halide, with the resultant formation of two liquid phases. Classic extraction methodology yields a recovery of at least 90 percent, preferably at least 95 percent, and most preferably 100 percent, of aqueous 2,3-epoxypropyltrialkylammonium halide, based on theoretical yield. This aqueous phase has a strong yellow color. The other phase is the solvent, which may be excess epihalohydrin or other aprotic liquid as defined hereinabove.

The resultant aqueous solution of 2,3-epoxypropyltrialkylammonium halide contains also unreacted epihalohydrin which, if not removed, can be the source of problems in subsequent production of in a finished cationic substrate product. Consequently, this residual epihalohydrin is removed from the solution of 2,3-epoxypropyltrialkylammonium halide by conventional methods such as solvent extraction or distillation.

Thus obtained aqueous solution of colored 2,3-epoxypropyltrialkylammonium halide is then treated with a small amount of alkali metal salt of hypochlorous acid, hypochlorous acid, or chlorine to eliminate or reduce its color according to the process of the present invention.

2,3-Epoxypropyltrialkylammonium halide produced in the method of the present invention is generally clear (water-white) in color or has reduced color. Color is measured by means of ASTM E 1209 (1993), termed as "Platinum-Cobalt Color, Test Method D 1209". This test method describes a procedure for the visual measurement of the color of essentially light colored liquids and is applicable only to materials in which the color-producing bodies present have light absorption characteristics nearly identical with those of the platinum-cobalt color standards used.

2,3-Epoxypropyltrimethylammonium halide, and particularly 2,3-epoxypropyltrimethylammonium chloride, obtained by the process of the present invention is useful for the production of cationic fibers and cationic substrates for color-sensitive applications such as, for example, the production of cationic starch for use in paper manufacture.

Useful substrates which can be imparted permanent cationic charge with 2,3-epoxypropyltrimethylammonium halide prepared according to the present invention include, but are not limited to, natural cellulosic materials such as starch, flour, guar gum, as well as synthetic materials such as cellulose ethers, polyvinyl alcohol and polymers.

Non-limiting examples of fibers which can be imparted permanent cationic charge with 2,3-epoxypropyltrimethylammonium halide prepared according to the present invention include: (i) natural and regenerated cellulosic fibers such as, for example, cotton, linen, and viscose rayon; (ii) natural and regenerated protein fibers such as, for example, wool, cashmere, and casein; (iii) regenerated fibers such as, for example, cellulose acetate, and cellulose triacetate; (iv) synthetic fibers such as, for example polyamide, polyester, and polyacrylonitrile.

The following examples are provided to more fully illustrate the present invention but are not intended to be, nor should they be construed as being, limiting in any way of the scope of the invention.

Preparation of 2,3-epoxypropyltrimethylammonium chloride

Step (1): 165 g of epichlorohydrin is charged to a Parr reactor and cooled to 13° C. Thereafter 21 g of trimethylamine is added with stirring and the reactants are allowed to react for six hours.

Step (2): To the product obtained in step (1) above is then added 23 g of water, resulting in two liquid phases. One phase is aqueous solution of 2,3-epoxypropyltrimethylammonium chloride, which has strong yellow color, measured as Platinum-Cobalt Color, Test Method D 1209, of 132. About 65 g of this aqueous phase is recovered. Also recovered is 139 g of excess epichlorohydrin.

Step (3): The aqueous solution of 2,3-epoxypropyltrimethylammonium chloride obtained in step (2) above is extracted with dichloromethane at 1:1 weight ratio six times to remove residual amounts of epichlorohydrin therefrom. The resulting aqueous solution of 2,3-epoxypropyltrimethylammonium chloride is strong yellow in color.

EXAMPLE 1

Sodium hypochlorite (0.1199 grams, 13 per cent active chlorine), providing about 575 ppm of active chlorine, is added, with stirring, to the aqueous solution of 2,3-epoxypropyltrimethylammonium chloride (26.978 grams) prepared as described hereinbefore and having the yellow color of 132 measured as Platinum-Cobalt Color, Test Method D 1209. Almost immediately, the Platinum-Cobalt Color, Test Method D 1209, is reduced to a reading of 9. Liquid chromatographic scans of 2,3-epoxypropyltrimethylammonium chloride, taken before and after addition of sodium hypochlorite, show no degradation of the product.

EXAMPLE 2

The procedure of Example 1 above is repeated except that 3.326 grams of 0.47 per cent aqueous chlorine solution (providing about 532 ppm of active chlorine) is added to the aqueous solution of 2,3-epoxypropyltrimethylammonium chloride (26.061 grams) prepared as described hereinbefore and having the yellow color of 134 measured as Platinum-Cobalt Color, Test Method D 1209. The Platinum-Cobalt Color, Test Method D 1209, of 2,3-epoxypropyltrimethylammonium chloride thus obtained is reduced to a reading of 22.

EXAMPLE 3

The procedure of Example 1 above is repeated except that 0.278 grams of 4.2 per cent hypochlorous acid (providing about 582 ppm of active chlorine) is added to the aqueous solution of 2,3-Epoxypropyltrimethylammonium chloride (26.817 grams) prepared as described hereinbefore and having the yellow color of 166 measured as Platinum-Cobalt Color, Test Method D 1209. The Platinum-Cobalt Color, Test Method D 1209, of 2,3-epoxypropyltrimethylammonium chloride thus obtained is reduced to a reading of 20.

EXAMPLE 4

Sodium hypochlorite (0.040 gram, 13 per cent active chlorine), providing about 196 ppm of active chlorine, is added, with stirring, to the aqueous solution of 2,3-epoxypropyltrimethylammonium chloride (26.58 grams) having the yellow color of 239 measured as Platinum-Cobalt Color, Test Method D 1209. Almost immediately, the Platinum-Cobalt Color, Test Method D 1209, of 2,3-epoxypropyltrimethylammonium chloride thus obtained is reduced to a reading of 120.

EXAMPLE 5

The procedure of Example 4 is repeated except that 0.083 gram of sodium hypochlorite (providing about 406 ppm of active chlorine) is used. The Platinum-Cobalt Color, Test Method D 1209, of 2,3-epoxypropyltrimethylammonium chloride thus obtained is reduced to a reading of 72.

EXAMPLE 6

The procedure of Example 4 is repeated except that 0.261 gram of sodium hypochlorite (providing about 1277 ppm of active chlorine) is used. The Platinum-Cobalt Color, Test Method D 1209, of 2,3-epoxypropyltrimethylammonium chloride thus obtained is reduced to a reading of 39.

EXAMPLE 7

The procedure of Example 4 is repeated except that 0.530 gram of sodium hypochlorite (providing about 2592 ppm of active chlorine) is used. The Platinum-Cobalt Color, Test Method D 1209, of 2,3-epoxypropyltrimethylammonium chloride thus obtained is reduced to a reading of 37.

EXAMPLE 8

The procedure of Example 4 is repeated except that 0.820 gram of sodium hypochlorite (providing about 4011 ppm of active chlorine) is used. The Platinum-Cobalt Color, Test Method D 1209, of 2,3-epoxypropyltrimethylammonium chloride thus obtained is reduced to a reading of 39.

EXAMPLE 9

The procedure of Example 4 is repeated except that 1.108 grams of sodium hypochlorite (providing about 5419 ppm of active chlorine) is used. The Platinum-Cobalt Color, Test Method D 1209, of 2,3-epoxypropyltrimethylammonium chloride thus obtained is reduced to a reading of 41.

EXAMPLE 10

The procedure of Example 4 is repeated except that 1.529 grams of sodium hypochlorite (providing about 7478 ppm of active chlorine) is used. The Platinum-Cobalt Color, Test Method D 1209, of 2,3-epoxypropyltrimethylammonium chloride thus obtained is reduced to a reading of 45.

EXAMPLE 11

The procedure of Example 4 is repeated except that 1.934 grams of sodium hypochlorite (providing about 9459 ppm of active chlorine) is used. The Platinum-Cobalt Color, Test Method D 1209, of 2,3-epoxypropyltrimethylammonium chloride thus obtained is reduced to a reading of 64.

EXAMPLE 12

The procedure of Example 4 is repeated except that 2.131 grams of sodium hypochlorite (providing about 10422 ppm of active chlorine) is used. The Platinum-Cobalt Color, Test Method D 1209, of 2,3-epoxypropyltrimethylammonium chloride thus obtained is reduced to a reading of 65.

EXAMPLE 13

The procedure of Example 4 is repeated except that 2.390 grams of sodium hypochlorite (providing about 11689 ppm of active chlorine) is used. The Platinum-Cobalt Color, Test Method D 1209, of 2,3-epoxypropyltrimethylammonium chloride thus obtained is reduced to a reading of 90.

EXAMPLE 14

The procedure of Example 4 is repeated except that 2.591 grams of sodium hypochlorite (providing about 12672 ppm of active chlorine) is used. The Platinum-Cobalt Color, Test Method D -209, of 2,3-epoxypropyltrimethylammonium chloride thus obtained is reduced to a reading of 125.

EXAMPLE 15

An Erlenmeyer flask containing solution of sodium sulfate (12.5 g) and 25 percent by weight sodium hydroxide (1.43 ml) in purified water (33 ml) is placed in a water bath kept at about 50° C. While stirring the solution with a magnetic stirrer, corn starch (22.16 g) is added to the flask. The resulting starch slurry is stirred for 10 minutes and then 2,3-epoxypropyltrimethylammonium chloride obtained in Example 1 above is added to the starch slurry in an amount to provide a theoretical degree of substitution of about 0.05. The reaction is allowed to proceed for 4 hours at a temperature of about 50° C. The pH of the starch reaction slurry is lowered to about pH=5–6 by the addition of 6N hydrochloric acid and then the resulting starch slurry is filtered through Whatman 113 filter paper under vacuum. The cationic starch thus obtained is washed with water (100 ml) three times and then dried in an oven at about 50° C. The starch was analyzed for nitrogen content. The analysis shows that it contained 0.4 percent nitrogen which is typical for these experimental conditions.

What is claimed is:

1. A process for eliminating or reducing color of an aqueous solution of 2,3-epoxypropyltrialkylammonium halide which process comprises treating a colored aqueous solution of 2,3-epoxypropyltrialkylammonium halide with an effective amount of an alkali metal salt of hypochlorous acid, hypochlorous acid or chlorine.

2. The process of claim 1 wherein an alkali metal salt of hypochlorous acid, hypochlorous acid or aqueous chlorine is used in an amount to provide from about 200 to about 15,000 ppm of active chlorine.

3. The process of claim 2 wherein an alkali metal salt of hypochlorous acid, hypochlorous acid or aqueous chlorine is used in an amount to provide from about 400 to about 10,000 ppm of active chlorine.

4. The process of claim 3 wherein an alkali metal salt of hypochlorous acid, hypochlorous acid or aqueous chlorine is used in an amount to provide from about 600 to about 5,000 ppm of active chlorine.

5. The process of claim 4 wherein an alkali metal salt of hypochlorous acid, hypochlorous acid or aqueous chlorine is used in an amount to provide from about 600 to about 2,500 ppm of active chlorine.

6. The process of any one of claims 1–5 wherein 2,3-epoxypropyltrialkylammonium halide is treated with sodium hypochlorite.

7. The process of any one of claims 1–5 wherein 2,3-epoxypropyltrialkylammonium halide is treated with hypochlorous acid.

8. The process of any one of claims 1–5 wherein 2,3-epoxypropyltrialkylammonium halide is treated with aqueous chlorine.

9. The process of any one of claims 1 to 5 wherein the aqueous solution of colored 2,3-epoxypropyltrialkylammonium halide is an aqueous solution of colored 2,3-epoxypropyltrimethylammonium chloride or an aqueous solution of colored 2,3-epoxypropyltrimethylammonium bromide.

10. The process of claim 1 wherein the aqueous solution of 2,3-epoxypropyltrialkylammonium halide having reduced color is further reacted with a substrate to produce a cationic substrate.

11. The process of claim 10 wherein the substrate is starch.

12. The process of claim 10 or claim 11 wherein 2,3-epoxypropyltrialkylammonium halide is 2,3-epoxypropyltrimethylammonium chloride.

* * * * *